United States Patent
Deno et al.

(10) Patent No.: US 10,206,652 B2
(45) Date of Patent: Feb. 19, 2019

(54) INTRACARDIAC IMAGING SYSTEM UTILIZING A MULTIPURPOSE CATHETER

(71) Applicant: St. Jude Medical, Atrial Filbrillation Division, Inc., St. Paul, MN (US)

(72) Inventors: D. Curtis Deno, Andover, MN (US); Anthony D. Hill, Minneapolis, MN (US); Hua Zhong, Pittsburgh, PA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1032 days.

(21) Appl. No.: 14/498,573

(22) Filed: Sep. 26, 2014

(65) Prior Publication Data

US 2015/0080715 A1 Mar. 19, 2015

Related U.S. Application Data (63) Continuation of application No. 12/982,968, filed on Dec. 31, 2010, now Pat. No. 8,900,150, which is a
(Continued)

(51) Int. Cl.
*A61B 5/06* (2006.01)
*A61B 8/12* (2006.01)
(Continued)

(52) U.S. Cl.
CPC .......... *A61B 8/0883* (2013.01); *A61B 5/0422* (2013.01); *A61B 5/06* (2013.01);
(Continued)

(58) Field of Classification Search
CPC ......... A61B 5/063; A61B 5/062; A61B 5/065; A61B 8/12; A61B 2034/2051; A61B 2034/2053; A61B 18/14; A61B 5/0422
See application file for complete search history.

(56) References Cited

U.S. PATENT DOCUMENTS

| | | |
|---|---|---|
| 4,951,682 A | 8/1990 | Petre |
| 5,279,299 A | 1/1994 | Imran |
| (Continued) | | |

FOREIGN PATENT DOCUMENTS

| | | |
|---|---|---|
| EP | 1929956 | 6/2008 |
| EP | 2077526 | 7/2009 |
| (Continued) | | |

OTHER PUBLICATIONS

Casas, O.; "In Vivo and In Situ Ischemic Tissue Characterization Using Electrical Impedance Spectroscopy"; Annals New York Academy of Sciences, vol. 873; Reference pp. 51-58; Publication Date: Apr. 1999.
(Continued)

*Primary Examiner* — Lee S Cohen
*Assistant Examiner* — Erin M Cardinal
(74) *Attorney, Agent, or Firm* — Dykema Gossett PLLC (57) ABSTRACT

A three dimensional physiological mapping system utilizing an intracardiac echo catheter capable of being located in six degrees of freedom by a visualization, navigation, or mapping system. An echocardiography image of the intracardiac echo catheter may be projected within a geometric model of the visualization, navigation, or mapping system where the location of the projected image is adjusted in response to user input identifying a structure present in the echocardiography image and the geometric model.

20 Claims, 7 Drawing Sheets

Related U.S. Application Data continuation-in-part of application No. 12/346,592, filed on Dec. 30, 2008, now abandoned, and a continuation-in-part of application No. 12/347,271, filed on Dec. 31, 2008, now Pat. No. 8,700,129, and a continuation-in-part of application No. 12/972,723, filed on Dec. 20, 2010, now Pat. No. 8,948,476.

(51) Int. Cl.
| | |
|---|---|
| *A61B 8/08* | (2006.01) |
| *A61B 5/042* | (2006.01) |
| *A61B 8/00* | (2006.01) |
| A61B 5/04 | (2006.01) |
| A61B 18/14 | (2006.01) |
| A61B 18/00 | (2006.01) |
| A61B 5/00 | (2006.01) |
| A61B 34/20 | (2016.01) |

(52) U.S. Cl.
CPC .............. *A61B 5/061* (2013.01); *A61B 5/063* (2013.01); *A61B 8/12* (2013.01); *A61B 8/463* (2013.01); *A61B 8/5238* (2013.01); *A61B 34/20* (2016.02); A61B 5/7217 (2013.01); A61B 18/14 (2013.01); A61B 2018/00755 (2013.01); A61B 2018/00839 (2013.01); A61B 2018/00875 (2013.01); A61B 2034/2051 (2016.02); A61B 2034/2053 (2016.02); A61B 2562/0209 (2013.01); A61B 2562/046 (2013.01); Y10S 128/916 (2013.01)

(56) References Cited

U.S. PATENT DOCUMENTS

| | | | | |
|---|---|---|---|---|
| 5,295,484 | A | * | 3/1994 | Marcus ............... A61B 5/042 600/439 |
| 5,297,549 | A | | 3/1994 | Beatty |
| 5,311,866 | A | | 5/1994 | Kagan et al. |
| 5,341,807 | A | | 8/1994 | Nardella |
| 5,391,199 | A | | 2/1995 | Ben-Haim |
| 5,409,000 | A | | 4/1995 | Imran |
| 5,447,529 | A | | 9/1995 | Marchlinski |
| 5,462,545 | A | | 10/1995 | Wang et al. |
| 5,546,940 | A | | 8/1996 | Panescu |
| 5,546,951 | A | | 8/1996 | Ben-Haim |
| 5,553,611 | A | | 9/1996 | Budd et al. |
| 5,562,721 | A | | 10/1996 | Marchlinski |
| 5,579,764 | A | * | 12/1996 | Goldreyer ............ A61B 5/0422 600/374 |
| 5,643,255 | A | | 7/1997 | Organ |
| 5,662,108 | A | | 9/1997 | Budd |
| 5,673,704 | A | | 10/1997 | Marchlinski |
| 5,697,377 | A | | 12/1997 | Wittkampf |
| 5,702,386 | A | | 12/1997 | Stern et al. |
| 5,704,361 | A | * | 1/1998 | Seward ............... A61B 8/06 128/916 |
| 5,713,946 | A | | 2/1998 | Ben-Haim |
| 5,817,022 | A | * | 10/1998 | Vesely ............... G01S 15/66 128/916 |
| 5,823,955 | A | | 10/1998 | Kuck |
| 5,836,875 | A | * | 11/1998 | Webster, Jr. ......... A61B 5/0422 600/374 |
| 5,836,990 | A | | 11/1998 | Li |
| 5,904,653 | A | | 5/1999 | Hatfield |
| 5,921,923 | A | | 7/1999 | Kuck |
| 5,944,712 | A | | 8/1999 | Frassica |
| 5,957,842 | A | | 9/1999 | Littmann |
| 5,983,126 | A | | 11/1999 | Wittkampf |
| 5,999,840 | A | | 12/1999 | Grimson et al. |
| 6,048,329 | A | * | 4/2000 | Thompson ......... A61B 18/1492 600/374 |
| 6,049,622 | A | | 4/2000 | Robb et al. |
| 6,091,995 | A | | 7/2000 | Ingle |
| 6,139,498 | A | | 10/2000 | Katsman |
| 6,200,314 | B1 | | 3/2001 | Sherman |
| 6,216,027 | B1 | * | 4/2001 | Willis ............... A61B 5/0422 600/424 |
| 6,235,018 | B1 | | 5/2001 | LePivert |
| 6,240,307 | B1 | | 5/2001 | Beatty et al. |
| 6,289,239 | B1 | | 9/2001 | Panescu |
| 6,304,776 | B1 | | 10/2001 | Muntermann |
| 6,556,695 | B1 | | 4/2003 | Packer |
| 6,574,498 | B1 | | 6/2003 | Gilboa |
| 6,584,343 | B1 | | 6/2003 | Ransbury et al. |
| 6,603,996 | B1 | | 8/2003 | Beatty et al. |
| 6,612,992 | B1 | * | 9/2003 | Hossack ............. A61B 8/12 600/467 |
| 6,640,119 | B1 | | 10/2003 | Budd et al. |
| 6,647,617 | B1 | | 11/2003 | Beatty et al. |
| 6,728,562 | B1 | | 4/2004 | Budd et al. |
| 6,826,420 | B1 | | 11/2004 | Beatty et al. |
| 6,826,421 | B1 | | 11/2004 | Beatty et al. |
| 6,895,267 | B2 | | 5/2005 | Panescu |
| 6,918,906 | B2 | | 7/2005 | Long et al. |
| 6,990,370 | B1 | | 1/2006 | Beatty et al. |
| 7,263,397 | B2 | | 8/2007 | Hauck |
| 7,426,256 | B2 | | 9/2008 | Rasche |
| 7,505,810 | B2 | | 3/2009 | Harley et al. |
| 7,604,601 | B2 | * | 10/2009 | Altmann ............. A61B 5/042 600/437 |
| 7,844,319 | B2 | * | 11/2010 | Susil ............... A61B 5/055 600/373 |
| 8,041,413 | B2 | | 10/2011 | Barbagli |
| 8,213,693 | B1 | | 7/2012 | Li |
| 8,611,983 | B2 | | 12/2013 | Glossop |
| 2002/0151793 | A1 | | 10/2002 | Geiser et al. |
| 2002/0188194 | A1 | | 12/2002 | Cosman |
| 2003/0013958 | A1 | | 1/2003 | Govari et al. |
| 2003/0063781 | A1 | | 4/2003 | Philomin |
| 2003/0065271 | A1 | | 4/2003 | Khoury |
| 2003/0093067 | A1 | | 5/2003 | Panescu |
| 2003/0130576 | A1 | | 7/2003 | Seeley |
| 2003/0163176 | A1 | | 8/2003 | Bae |
| 2003/0163178 | A1 | | 8/2003 | Davison |
| 2004/0078036 | A1 | | 4/2004 | Keidar |
| 2004/0097805 | A1 | | 5/2004 | Verard et al. |
| 2004/0142485 | A1 | | 7/2004 | Flower |
| 2004/0220471 | A1 | | 11/2004 | Schwartz |
| 2004/0254437 | A1 | | 12/2004 | Hauck et al. |
| 2005/0065434 | A1 | | 3/2005 | Bavaro |
| 2005/0203394 | A1 | * | 9/2005 | Hauck ............... A61B 5/0422 600/437 |
| 2005/0246130 | A1 | | 11/2005 | Spicer |
| 2006/0058588 | A1 | * | 3/2006 | Zdeblick ............. A61B 5/0422 600/300 |
| 2006/0122514 | A1 | * | 6/2006 | Byrd ............... A61B 5/06 600/466 |
| 2007/0016007 | A1 | * | 1/2007 | Govari ............... A61B 5/0538 600/424 |
| 2007/0027392 | A1 | | 2/2007 | Schwartz |
| 2007/0073179 | A1 | | 3/2007 | Afonso |
| 2007/0167801 | A1 | | 7/2007 | Webler et al. |
| 2007/0255136 | A1 | | 11/2007 | Kristofferson et al. |
| 2007/0299353 | A1 | | 12/2007 | Harlev |
| 2008/0085043 | A1 | | 4/2008 | Watanabe et al. |
| 2008/0119727 | A1 | * | 5/2008 | Barbagli ............. A61B 5/06 600/424 |
| 2008/0137927 | A1 | | 6/2008 | Altmann et al. |
| 2008/0177183 | A1 | | 7/2008 | Courtney |
| 2008/0221425 | A1 | | 9/2008 | Olson |
| 2008/0221440 | A1 | | 9/2008 | Iddan |
| 2008/0249395 | A1 | | 10/2008 | Shachar |
| 2008/0287803 | A1 | | 11/2008 | Li et al. |
| 2008/0287805 | A1 | * | 11/2008 | Li ............... A61B 8/0833 600/471 |
| 2008/0300589 | A1 | | 12/2008 | Paul |
| 2009/0107230 | A1 | | 4/2009 | Okcay |
| 2009/0177089 | A1 | | 7/2009 | Govari et al. |
| 2009/0264777 | A1 | | 10/2009 | Markowitz |
| 2009/0275827 | A1 | | 11/2009 | Aiken |
| 2009/0292206 | A1 | | 11/2009 | Sato |

(56) References Cited

U.S. PATENT DOCUMENTS

| | | |
|---|---|---|
| 2009/0292209 A1 | 11/2009 | Hadjicostis |
| 2010/0099991 A1 | 4/2010 | Snyder |
| 2010/0165672 A1 | 7/2010 | Li |
| 2010/0168558 A1 | 7/2010 | Olson |
| 2010/0168569 A1 | 7/2010 | Sliwa |
| 2010/0168572 A1 | 7/2010 | Sliwa |
| 2010/0172554 A1 | 7/2010 | Kassab |
| 2010/0312095 A1 | 12/2010 | Jenkins |
| 2010/0312096 A1 | 12/2010 | Guttman |
| 2011/0123088 A1 | 5/2011 | Sebok |
| 2011/0125150 A1 | 5/2011 | Deno et al. |
| 2011/0142316 A1 | 6/2011 | Wang |
| 2011/0184274 A1* | 7/2011 | Rosenberg ........... A61B 5/0536 600/424 |
| 2011/0224655 A1 | 9/2011 | Asirvatham |
| 2011/0230896 A1 | 9/2011 | Wallace |
| 2011/0319765 A1 | 12/2011 | Gertner |
| 2012/0095357 A1 | 4/2012 | Tran |
| 2012/0158011 A1 | 6/2012 | Sandhu |
| 2012/0165672 A1 | 6/2012 | Hill |
| 2012/0172724 A1 | 7/2012 | Hill |
| 2013/0226169 A1 | 8/2013 | Miller et al. |
| 2013/0274582 A1* | 10/2013 | Afonso ................ A61B 5/0422 600/374 |
| 2013/0310674 A1 | 11/2013 | Deno et al. |

FOREIGN PATENT DOCUMENTS

| | | |
|---|---|---|
| JP | H10-33535 | 2/1998 |
| WO | 2000/007501 | 2/2000 |
| WO | 2008/042423 | 4/2008 |

OTHER PUBLICATIONS

European Search Report in EP Application No. 09015744.7. (dated Jun. 4, 2010).
Ju, Tao; "Mean Value Coordinates for Closed Triangular Meshes"; ACM Transactions on Graphics 24(3); Reference pp. 561-566; Publication Date: Jul. 2005.
Wittkampf, Fred H.; "LocaLisa: New Technique for Real-Time 3-Dimensional localization of regular intracardiac electrodes"; Circulation—Journal of the American Heart Association; Reference pp. 1312-1317; Publication Date: Mar. 1999.
Author: Orr, Mark J Title: Introduction to radial basis function networks Reference pp. 1-67 Publication Date: Apr. 1996.
Bar-Itzhack, Itzhack Y.; "New Method for Extracting the Quaternion from a Rotation Matrix"; J. Guidance, vol. 23, No. 6, Engineering Notes; Reference pp. 1085-1087; Publication Date: Nov. 2000.
Cao, Hong; "FEM Analysis of Predicting Electrode-Myocardium Contact from RF Cardiac Catheter Ablation System Impedance"; IEEE Transactions on Biomedical Engineering, vol. 49, No. 6; Reference pp. 520-526; Publication Date: Jun. 2002.
Cao, Hong; "Using Electrical Impedance to Predict Catheter-Endocardial Contact during RF Cardiac Ablation"; IEEE Transactions on Biomedical Engineering, vol. 49, No. 3; Reference pp. 247-253; Publication Date: Mar. 2002.
Chan, R.C. et al., "Intraprocedural fusion of electroanatomical maps (EAM) with imaging data based on rapidly-sampled volumetric point clouds from continuous EAM catheter tracking", Proceedings of SPIE, vol. 6509, Mar. 6, 2007.
Chui, Haili; "A new algorithm for non-rigid point matching"; IEEE Conference on Computer Vision and pattern, vol. 2; Reference pp. 44-51; Publication Date: Jun. 2000.
Cinca, Juan; "Changes in Myocardial Electrical Impedance Induced by Coronary Artery Occlusion in Pigs with and without Preconditioning"; Circulation; Publication Date: Nov. 1997.
del Rio, Carlos L.; "Early time course of myocardial electrical impedance during acute coronary artery occlusion in pigs, dogs, and humans"; Citation: Journal of Applied Physiology, vol. 99; Reference pp. 1576-1581 Publication Date: Jun. 15, 2005.
Fallert, MA; "Myocardial electrical impedance mapping of ischemic sheep hearts and healing aneurysms"; Citation: Circulation, vol. 87, No. 1; Reference pp. 199-207; Publication Date: Jan. 1993.
Fitzpatrick, Michael J; "Handbook of medical imaging (vol. 2, Medical image processing and analysis" SPIE—The international society for optical engineering; Reference pp. 451-514; Publication Date: Jun. 2000.
Gepstein, Lior; "A novel method for nonfluoroscopic catheter-based electroanatomical mapping of the heart"; Circulation; Publication Date: Mar. 1997.
Haines, DE; "Observations on electrode-tissue interface temperature and effect on electrical impedance during radiofrequency ablation of ventricular myocardium"; Circulation, vol. 82, No. 3; Reference pp. 1034-1038; Publication Date: Sep. 1990.
Hoffmann, Ellen; "Biophysical parameters of radiofrequency catheter ablation"; Citation: International Journal of Cardiology, vol. 37; Reference pp. 213-222; Publication Date: Dec. 1992.
Horn, Berthold K.P.; "Closed-form solution of absolute orientation using unit quaternions"; Journal of teh Optical Society of America, vol. 4; Reference pp. 629-642; Publication Date: Apr. 1987.
Howie, Michael B.; "An Evaluation of a New Two-Electrode Myocardial Electrical Impedance Monitor for Detecting Myocardial Ischemia"; Anesth. Analg, vol. 92:12-8; Reference pp. 12-18; Publication Date: Jan. 2001.
International Search Report and Written Opinion in PCT Application No. PCT/US2011/063591 (dated Apr. 16, 2012).
Kearsley, Simon; "On the orthogonal transformation used for structural comparisons"; Acta Crystallographica Vo. A45; Reference pp. 208-210; Publication Date: Feb. 1989.
Ko, Wen-Chin; "New Method for Predicting Efficiency of Heating by Measuring Bioimpedance During Radiofrequency Catheter Ablation in Humans"; Journal of Cardiovascular Electrophysiology, vol. 12, No. 7; Reference pp. 819-823; Publication Date: Jul. 2001.
Lang, Christopher C.E.; "Endocardial impedance mapping during circumferential pulmonary vein ablation of atrial fibrillation differentiates between atrial and venous tissue"; Heart Rhythm Society, vol. 3, No. 2; Reference pp. 171-178; Publication Date: Feb. 2006.
Packer, Douglas L. et al., "New generation of electro-anatomic mapping: full intracardiac ultrasound image integration", Europace, vol. 10, No. Supplement 3, Nov. 1, 2008.
Ragheb, T.; "The Impedance of a Spherical Monopolar Electrode"; Annals of Biomedical Engineering, vol. 20; Reference pp. 617-627; Publication Date: Nov. 1992.
Ragheb, T.; "The Polarization Impedance of Common Electrode Metals Operated at Low Current Density"; Annals of Biomedical Engineering, vol. 19, Issue 2; Reference pp. 151-163; Publication Date: Mar. 1991.
Salazar, Yolocuauhtli; "Effect of electrode locations and respiration in the characterization of myocardial tissue using a transcatheter impedance method"; Physiological Measurement, No. 25; Reference pp. 1095-1103; Publication Date: Oct. 2004.
Salazar, Yolocuauhtli; "Transmural Versus Nontransmural In Situ Electrical Impedance Spectrum for Healthy, Ischemic, and Healed Myocardium"; IEEE Transactions on Biomedical Engineering, vol. 51 No. 8; Reference pp. 1421-1427; Publication Date: Aug. 2004.
Schwartzman, David; "Electrical Impedance Properties of Normal and Chronically Infarcted Left Ventricular Myocardium"; Journal of Interventional Cardiac Electrophysiology, vol. 3; Reference pp. 213-224; Publication Date: Oct. 1999.
Strickberger, S. Adam; "Relation between impedance and endocardial contact during radiofrequency catheter ablation"; American Heart Journal, vol. 1298, No. 2; Reference pp. 226-229; Publication Date: Aug. 1994.
Supplementary European Search Report in EP Application No. 11850605.4 (dated Feb. 25, 2015).
Title: 3D Slicer Citation: 3D Slicer "Modules: Fiducials—Documentation—3.2" (2008).
Wolf, Tamir; "Three-dimensional endocardial impedance mapping: a new approach for myocardial infarction assessment"; AJP—Heart and Circulatory Physiology, vol. 280; Reference pp. 179-188; Publication Date: Jan. 2001.
Zheng, Xiangsheng; "Electrode Impedance: An Indicator of Electrode-Tissue Contact and Lesion Dimensions During Linear Ablation";

(56) References Cited

OTHER PUBLICATIONS

Journal of Interventional Cardiac Electrophysiology 4; Reference pp. 645-654; Publication Date: Dec. 2000.
Author: Cho, Sungbo Title: Design of electrode array for impedance measurement of lesions in arteries Citation: Physiol. Meas. 26 S19-S26 Publication Date: Mar. 29, 2005.
Author: Gales, Rosemary Title: Use of bioelectrical impedance analysis to assess body composition of seals Citation: Marine Mammal Science, vol. 10, Issue 1, Abstract Publication Date: Aug. 26, 2006.
Author: Masse, Stephane Title: A Three-dimensional display for cardiac activation mapping Citation: Pace, vol. 14 Publication Date: Apr. 1991.
Avitall, Boaz; "The Effects of Electrode-Tissue Contact on Radiofrequency Lesion Generation"; PACE, vol. 20; Reference pp. 2899-2910; Publication Date: Dec. 1997.
Chakraborty, D. P.; "ROC curves predicted by a model of visual search"; Institute of Physics Publishing, Phys. Med. Biol. 51; Reference pp. 3463-3482; Publication Date: Jul. 6, 2006.
Dumas, John H.; "Myocardial electrical impedance as a predictor of the quality of RF-induced linear lesions"; Physiological Measurement, vol. 29; Reference Pages: Abstract only; Publication Date: Sep. 17, 2008.
Fenici, R. R.; "Biomagnetically localizable multipurpose catheter and method for MCG guided intracardiac electrophysiology, biopsy and ablation of cardiac arrhythmias"; International Journal of Cardiac Imaging 7; Reference pp. 207-215; Publication Date: Sep. 1991.
Gao et al. "Computer-Assisted Quantitative Evaluation of Therapeutic Responses for Lymphoma Using Serial PET/CT Imaging", Academic Radiology, vol. 17, No. 4, Apr. 2010.
He, Ding Sheng; "Assessment of Myocardial Lesion Size during In Vitro Radio Frequency Catheter Ablation"; IEEE Transactions on Biomedical Engineering, vol. 50, No. 6; Reference pp. 768-776; Publication Date: Jun. 2003.
Himel, Herman D.; "Development of a metric to assess completeness of lesions produced by radiofrequency ablation in the heart"; Dept. of Biomedical Engineering, University of NC, Chapel Hill; Reference pp. i-xvii; 1-138; Publication Date: 2006.
Holmes, Douglas; "Tissue Sensing Technology Enhances Lesion Formation During Irrigated Catheter Ablation"; HRS; Reference Pages: Abstract only; Publication Date: 2008.
International Search Report and Written Opinion in PCT Application No. PCT/US2008/084194 (dated Feb. 5, 2009).
International Search Report and Written Opinion in PCT Application No. PCT/US2011/047235 (dated Dec. 14, 2011).
Supplementary European Search Report issued in EP Patent Application No. 11842330.0 (dated Jan. 20, 2014).
Title: International Search Report and Written Opinion of the International Searching Authority Citation: PCT/US2006/061714 Publication Date: Sep. 22, 2008.

* cited by examiner

INTRACARDIAC IMAGING SYSTEM UTILIZING A MULTIPURPOSE CATHETER

CROSS-REFERENCE TO RELATED APPLICATIONS

This application is a continuation of U.S. application Ser. No. 12/982,968, filed 31 Dec. 2010 (the '968 application), now U.S. Pat. No. 8,900,150; which is a continuation-in-part of U.S. application Ser. No. 12/346,592, filed Dec. 30, 2008 (the '592 application), now abandoned; U.S. application Ser. No. 12/347,271, filed Dec. 31, 2008 (the '271 application), now U.S. Pat. No. 8,700,129; and U.S. application Ser. No. 12/972,723, filed Dec. 20, 2010 (the '723 application), now U.S. Pat. No. 8,948,476. The '968 application, '592 application, '271 application, and '723 application are each hereby incorporated by reference as though fully set forth herein.

BACKGROUND OF THE INVENTION a. Field of the Invention

The present disclosure relates to intracardiac catheter location and imaging, and among other things, the present disclosure relates to the combination of intracardiac images from multiple imaging modalities and utilizing structures present in each image to more accurately produce composite images.

b. Background Art

Electrophysiology catheters are used in a variety of diagnostic and therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments or death.

In a typical procedure, a catheter and sheath are manipulated through a patient's vasculature to a patient's heart. The catheter carries one or more electrodes which may be used for mapping, ablation, or other treatments. Once positioned, treatment may include radio frequency (RF) ablation, cryoablations, lasers, chemicals, high-intensity focused ultrasound, etc. An ablation catheter imparts energy to the cardiac tissue to create a lesion that disrupts undesirable electrical pathways, thereby limiting or preventing stray electric signals leading to arrhythmias. The position of the ablation catheter within the heart can directly affect the physician's ability to accurately and effectively perform an ablation procedure.

Two catheter based imaging modalities are commonly used in electrophysiology procedures, the first being intracardiac echo ("ICE") that produces an echo image displaying structures within an echo plane emitted from the catheter. Traditionally, ICE catheters do not contain electrodes and their orientation and position are determined with reference to landmark structures visible in the echo image in conjunction with other imaging modalities such as fluoroscopy, magnetic resonance imaging ("MRI"), or computed tomography ("CT") models.

Location of the ICE catheter using fluoroscopy can involve several drawbacks, the first being that the images produced through fluoroscopy are two dimensional and include overlay of all intervening tissue and bone structures, which can obstruct the areas of interest. Without a third dimension, navigation and location of the ICE catheter can be challenging. The second drawback is the patient's exposure to doses of radiation in the course of a procedure.

Both MRI and CT devices are capable of producing a geometric model of cardiac structures, yet neither can do so in real time during a procedure utilizing an ICE catheter. Instead, both create a model which can serve as a general reference in which the position of the ICE catheter can be located generally, but may not provide the desired specificity for use during cardiac procedures. Thus, it can be difficult to place an ICE catheter in the position and orientation needed to generate an image of a specific structure of interest.

The second imaging modality commonly employed is a three dimensional physiological visualization, navigation, or mapping system that uses electrical or magnetic fields to determine the position and orientation of a catheter within the heart. One example of such as visualization, navigation, or mapping system is the EnSite NavX system comprising hardware and software available from St. Jude Medical of St. Paul, Minn. This system creates a geometric model by tracking the electrical impedance of a mapping catheter in three different directions. The three dimensional map is then constructed with reference to a static reference electrode. The reference electrode allows the mapping device to compensate for voluntary shifting by the patient, such as from localized discomfort, and to compensate for involuntary movement, such as breathing, thereby creating a more stable model.

However, electrical navigational fields are not assured to be homogeneous or isotropic, so it is common for these geometric models to face the challenge of spatial distortion. Further complicating the location of ICE catheters and the images they produce is the fact that any variations in the positioning and orientation of the electrodes with respect to the ultrasound transducer result in apparent translational and rotational positioning errors. An angular misalignment resulting from a rotational positioning error causes a spatial discrepancy between the actual and displayed locations. The discrepancy from angular misalignment increases the further from the ultrasound transducer an object is located. Thus, even moderate rotational error can result in significant positioning error for structures appearing at the edge of an echo image.

It is well known that intracardiac echo catheters provide images of cardiac structures and, under some conditions, other intracardiac catheters. The metal electrodes present on intracardiac catheters are very echogenic and produce bright signatures in echo images, particularly when the catheter shaft is not axially aligned with the echo plane or when the catheter shaft lies in the plane of the echo beam and is oriented perpendicular to it. However, identification of another catheter alone is seldom sufficient to locate the ICE catheter and may not allow the accurate projection of the ICE echo image into a geometric model created with electric or magnetic field modeling.

The inventors herein have thus recognized a need for a system and method for precise and real-time location of ICE catheters and the images they produce within geometric models of the heart, or within the heart itself, to allow physicians to easily obtain ICE images of cardiac structures and/or other intracardiac catheters of interest to allow accurate and effective therapeutic treatment.

BRIEF SUMMARY OF THE INVENTION

One advantage of apparatus and method described, depicted and claimed herein relates to the reliable location and orientation of an intracardiac echo catheter by a position sensing and mapping system, which may be used to accurately project an intracardiac echocardiography image into a geometric model.

An intracardiac echo catheter that consists of a handle, a long flexible shaft, a distal deflectable section, and at the tip a short rigid section containing a sensor array. The sensor array contains an ultrasound transducer and at least three electrodes configured to produce a response signal when placed within an electric field of a visualization, navigation, or mapping system. The ultrasound transducer allows the catheter to generate intracardiac echocardiography images. The electrodes also allow the distal end of the catheter to generate electrocardiogram signals observed by the electrodes in response to cardiac structures in close proximity, which may allow a user to determine the location of the sensor array, and thus the distal tip of the catheter, within the heart.

A visualization, navigation, or mapping system may use the response signals from the electrodes within the catheter to locate the catheter, and thereby the intracardiac echocardiography images it produces, within a geometric model maintained by the system. The visualization, navigation, or mapping system may also detect and locate within the geometric model electrodes present on other medical devices in the body cavity. When these other electrodes appear within the intracardiac echocardiography image, position data from the visualization, navigation, or mapping system and the intracardiac echocardiography data may be combined to form a fiducial point pair. Fiducial point pairs allow calibration steps to be performed so as to more accurately display an intracardiac echocardiography image within the geometric model of the system. Calibration steps may be applied after each fiducial point pair is identified, or after a group has been identified. In either case, the more fiducial point pairs that are known the more effective and broadly applicable the calibration step becomes.

The foregoing and other aspects, features, details, utilities, and advantages of the present disclosure will be apparent from reading the following description and claims, and from reviewing the accompanying drawings.

DETAILED DESCRIPTION OF THE INVENTION

Figure 1:
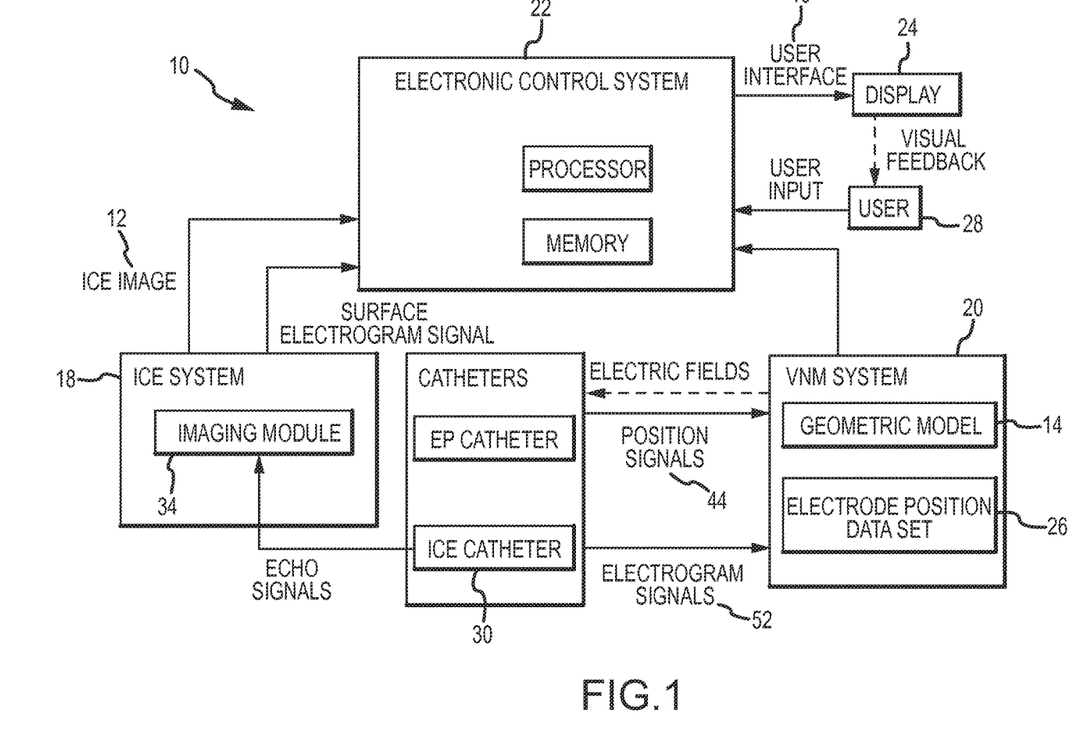
FIG. 1 is a block diagram illustrating the functional interrelationship of the components of the system in accordance with the present disclosure.

Referring now to the drawings wherein like reference numerals are used to identify identical components in the various views, FIG. 1 illustrates one exemplary embodiment of a system 10 configured to locate and orient an intracardiac echocardiography image 12 (ICE image), within a geometric model 14 of the heart, and to further generate a user interface 16 for receiving user input allowing more accurate orientation of the ICE image 12. The system 10 according to an embodiment of the present disclosure comprises an intracardiac echo imaging system 18 (ICE system), a visualization, navigation, or mapping system 20 ("VNM" system), an electronic control system (ECS) 22, and a display 24, each of which are described in detail below. The ECS 22 may be configured to receive an ICE image 12 produced by the ICE system 18 and the ECS 22 may further be configured to acquire a geometric model 14 of the heart and an electrode position data set 26 from the VNM system 20. ECS 22 may be further configured to position the ICE image 24 within the geometric model 14 using the electrode position data set 26 and to generate a user interface 16 allowing a user 28 to identify structures appearing within both the ICE image 12 and the geometric model 14. These commonly identified structures may be used by the ECS 22 to perform one or more calibration steps adjusting the position of the ICE image 12 within the geometric model 14.

The ICE image 12 must be capable of being located with six degrees of freedom (i.e., x, y, and z positions as well as pitch, roll, and yaw) within the geometric model 14 of the VNM system 20 to facilitate the accurate projection of the ICE image 12 into the geometric model 14 maintained by the by the VNM system 20.

The VNM system 20 may be electrically coupled (i.e., via wires or wirelessly) to the ECS 22, and may be configured to provide many advanced features, such as visualization, navigation, and mapping support and positioning (i.e., determine a position and orientation (P&O)) of a sensor-equipped medical device, for example, a P&O of a distal tip portion of a catheter.

The VNM system 20 of one embodiment is based on the principal that when electrical currents are passed through the thorax of a body a voltage drop occurs through resistive media such as the heart and blood and this voltage drop can be measured and used to determine the position of a medical device within the body. The system includes three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of a coordinate system for the navigation system. Very low sinusoidal currents are driven through each pair of patch electrodes and voltage measurements for one or more electrodes associated with the medical device are obtained. The measured voltages are a function of the distance of the device electrodes from the patch electrodes. The measured voltages are compared to the potential at the reference electrode and a position of the device electrodes within the coordinate system of the navigation system is determined.

The VNM system 20 may also maintain a geometric model 14 of body structures (e.g., the heart) based on the P&O data acquired from a mapping electrode maneuvered within the body cavity to define the structures of the body cavity. As generally illustrated in FIG. 1, the VNM system 20 may also generate and track the P&O of electrophysiology procedure (EP) catheters and other medical devices within the geometric model 14 where those medical devices contain a sensor configured to generate a signal in response to the sinusoidal currents of the VNM system 20, such as electrodes. The positions of the tracked electrodes may be included in the electrode position data set 26. Such functionality may be provided as part of a larger visualization, navigation, or mapping system, for example, an EnSite Velocity™ system running a version of NavX™ software commercially available from St. Jude Medical, Inc., and as also seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present application, and hereby incorporated by reference in its entirety.

Figure 2:
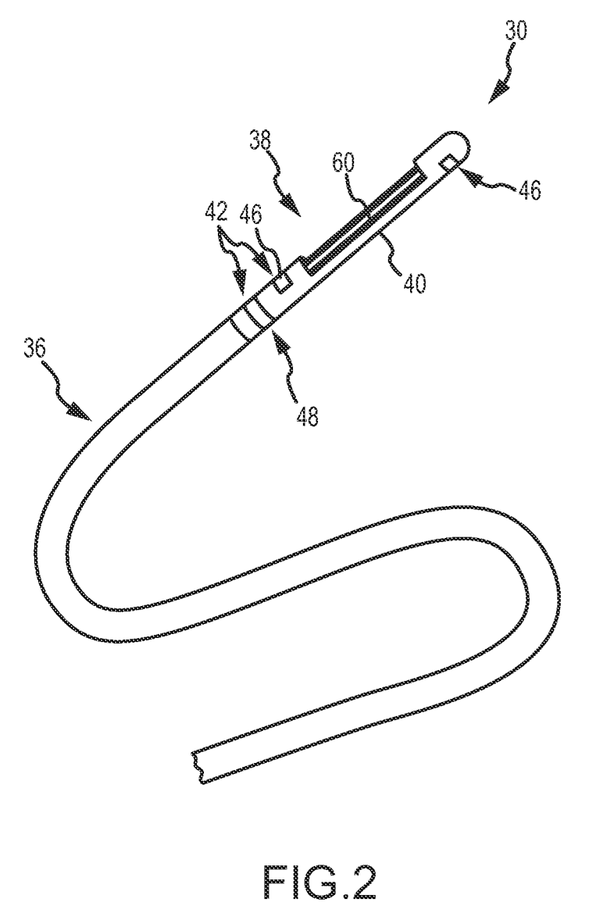
FIG. 2 generally illustrates the shaft and distal end of a multiple electrode intracardiac echo catheter in accordance with the present disclosure.

The ICE system 18 may comprise an intracardiac echo catheter 30 (ICE catheter) for sending and receiving ultrasound energy in an echo plane 32 (shown in FIG. 5a) and an imaging module 34 for generating a two dimensional echo image 12 representative of the received ultrasound energy. In an alternative embodiment, the ICE system 18 can further comprise a plurality of surface patch electrodes (not shown) that are applied to the external surfaces of the body and which generate surface electrocardiograms during a diagnostic or therapeutic procedure. As shown in FIG. 2, the ICE catheter 30 comprises a long flexible body member 36 and a sensor array 38 containing an ultrasound transducer 40 and a number of electrodes 42. The sensor array 38 is fixed to the end of the flexible body member 36 and may be inserted intravenously and navigated to the heart by manipulating the length of the flexible body member 36 extending outside the patient. The electrodes 42 may be responsive to an electric field and configured to generate a position response signal 44 when positioned within such a field. The position response signal 44 may be communicated to the VNM system 20 to generate P&O data locating the electrodes within the geometric model 14.

The electrodes 42 can be positioned distal or proximal to the ultrasound transducer 40, but in an embodiment are split, having at least one electrode 42 distal and at least one electrode 42 proximal. The electrodes 42 can take multiple forms, such as, by way of example, spot type electrodes, ring type electrodes, or partially masked electrodes. Spot type electrodes 46 have an exposed electrical contact surface limited to a portion of the circumference of the sensor array 38. Ring type electrodes 48 have an exposed electrode surface encompassing the full circumference of the sensor array 38. The form of the electrodes 42 affects how they are perceived by the VNM system 20, which is described in detail below. A spot electrode 46, ring electrode 48, or other electrode 42 may have a portion of its conductive surface insulated to create a partially masked electrode.

Figure 3:
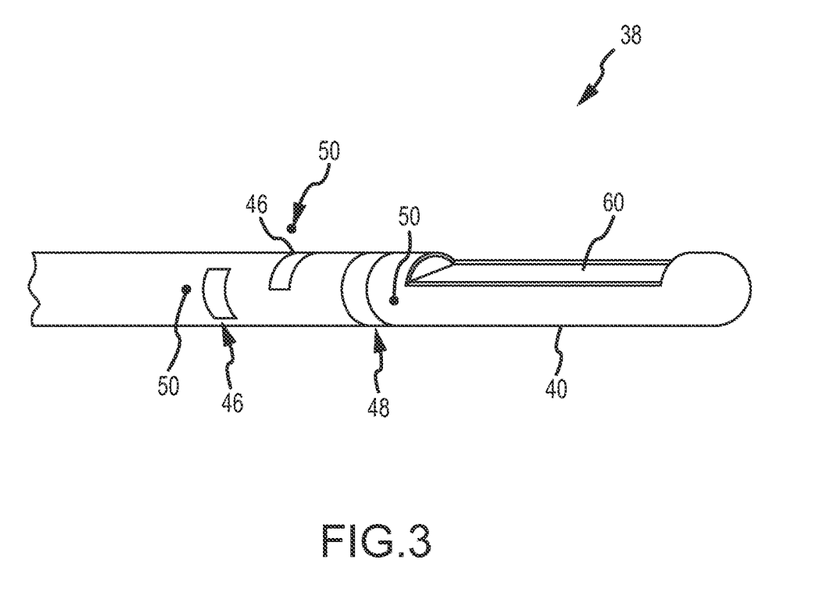
FIG. 3 generally illustrates an intracardiac echo transducer having electrodes disposed proximal to the ultrasonic transducer illustrating the centroid positions from an electrical and an echo catheter standpoint.

The electrical position 50 (dot) of an electrode does not necessarily coincide with the physical location of the electrode within the sensor array 38, which is generally illustrated with spot electrodes 46 and a ring electrode 48 in FIG. 3. The electrical position 50 of a spot electrode 46 as detected by a VNM system 20 may appear at twice the radial distance from the longitudinal axis of the sensor array 38. Ring electrodes 48 have an electrical position 50 appearing at the center of the ring (e.g., on the catheter's longitudinal axis). The electrical position 50 of the partially masked electrodes vary with the amount of masking, but generally partially masking a ring electrode 48 can cause it to be detected in a similar manner as a spot electrode 46 (i.e., the electrical position 50 shifts from the center of the ring).

Use of impedance-based electrodes 42 for positioning by a VNM system 20 rather than coil sensors responsive to a magnetic field can provide several advantages. Catheters 30 containing impedance-based electrodes 42 are commonly less complicated to manufacture as magnetic coil sensors involve small windings of very small wires. By contrast, impedance based electrodes are robust and typically welded to more moderately sized wires and crimped, swaged, or reflow secured to the outside of a catheter shaft. In addition, the intense magnetic fields required for magnetically-tracked coils have a tendency to cause interference on other medical electronics systems unless care is taken to coordinate with those other systems. The navigational fields, as sensed by the electrodes 42 and created by current driven patch electrodes, are much less prone to interfere with other medical systems. Furthermore, the electrodes 42 may be used for electrogram sensing and pacing.

Figure 4:
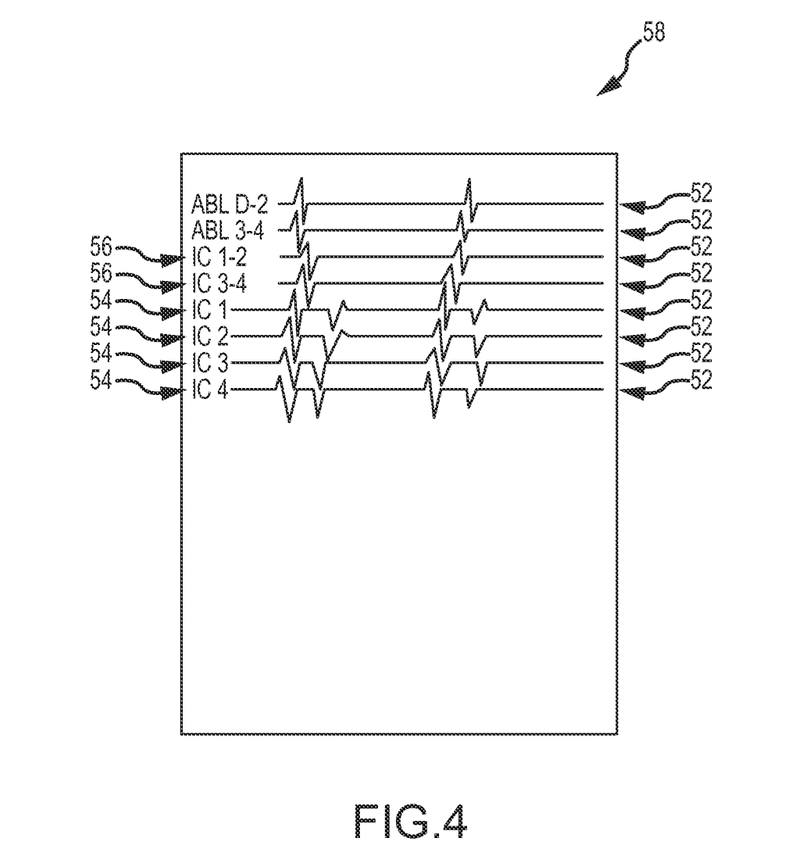
FIG. 4 illustrates a display of electrogram signals from multiple electrodes positioned within an intracardiac echo catheter in accordance with an embodiment of the present disclosure.

In addition to providing a position response signal 44 to locate the electrode 42 within the geometric model 14 of the VNM system 20, the electrodes 42 of the ICE catheter 30 or other EP catheters can also be used to produce electrogram signals. As depicted in FIG. 4, each electrode 42 produces an electrogram signal 52 representative of the electrical activity present in cardiac structures in close proximity to the electrode 42 that is received by the VNM system 20 and that may be communicated to the ECS 22. The electrogram signals 52 can be both unipole signals 54 and bipole signals 56. In an alternative embodiment, the ECS 22 may further receive surface electrogram signals (not shown) from electrode patches of the ICE system 18 attached to the external surfaces of the body. The ECS 22 may communicate to an external display device (e.g., a typical ECG device) received surface electrograms and/or electrogram signals 52 and the ECS 22 may be configured to generate an electrogram window 58 depicting surface electrogram signals and electrogram signals 52 independently on the display 24 or as part of an interface window 16.

Positioning electrodes 42 both proximal and distal to the ultrasound transducer 40 within the sensor array 38 of the ICE catheter 30 provides the clinician with an additional means for generally locating the ICE catheter 30 within the various cardiac chambers independent of the VNM system 20. The electrodes 42, and thus the ICE catheter 30, may be generally located within the heart solely through the electrogram signals 52 because different chambers of the heart have distinctive electrogram signals 52 well known to those skilled in the art. Of particular interest are the valve structures where atrial electrograms transition to ventricular signals and venous inflow sites where atrial electrograms are weak or absent. When an ICE catheter 30 is positioned such that the distal and proximal ends are in different cardiac chambers the electrogram signals 52 from electrodes 42 positioned distal to the ultrasound transducer 40 differ from the electrogram signals 52 from the electrodes 42 positioned proximal to the ultrasound transducer 40. Similarly, the position of the ICE catheter 30 can be approximated relative to myocardium when bipole signals 56 with large amplitudes are present. Positioning electrodes 42 on the back side of the ultrasound transducer 40 offer further resolution for electrogram analysis. ICE catheters 30 having electrodes 42 evenly spaced about the circumference of the sensor array 38 allows electrograms 52 of cardiac structures in close proximity to the ICE catheter 30 to be generated regardless of the particular orientation of the sensor array 38 relative to the cardiac structure.

Figure 5A:
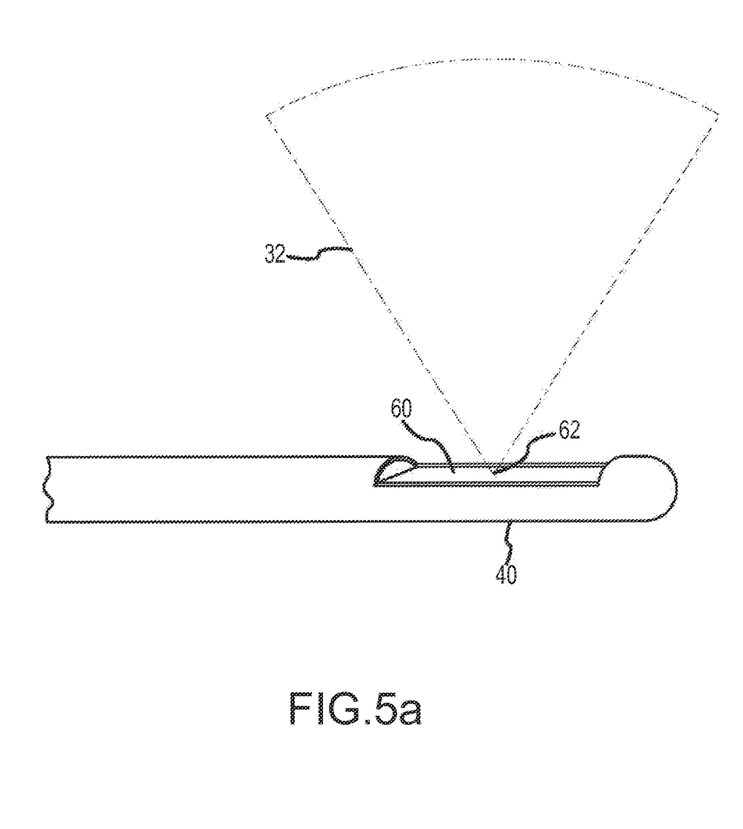
FIG. 5a generally illustrates the archetypal orientation of the echo plane to the echo transducer of an intracardiac echo catheter of an embodiment of the present disclosure.
Figure 5B:
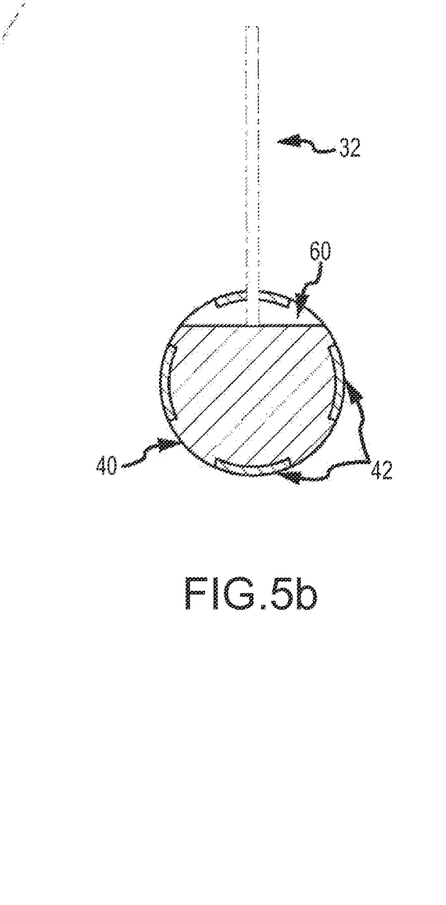
FIG. 5b is a cross-sectional view generally illustrating the archetypal orientation of the echo plane to the electrodes of the intracardiac echo catheter of an embodiment of the present disclosure.

The ICE system 18 of an embodiment consistent with the present disclosure may be configured to execute an imaging module 34 to generate a two dimensional ICE image 12 representative of structures intersected by the echo plane 32 emitted from the ultrasound transducer 40. The ICE image 12 may be represented by an image data set containing, for each pixel of the ICE image 12, a coordinate describing the position of a point (e.g., pixel) relative to the ultrasound transducer 40 and the color of the point. FIGS. 5a and 5b show an archetypal ultrasound transducer 40, having a transducer face 60 and an echo plane 32. The echo plane 32 being fan shaped and having an apex 62 at a known offset with respect to the centroid of the sensor array 38, the fan plane is aligned with the sensor array 28 and the fan angle bisector is perpendicular to the longitudinal axis of the sensor array 38. The echo plane 32 produced by actual ICE catheters 30 may deviate from the archetypal arrangement.

Figure 6A:
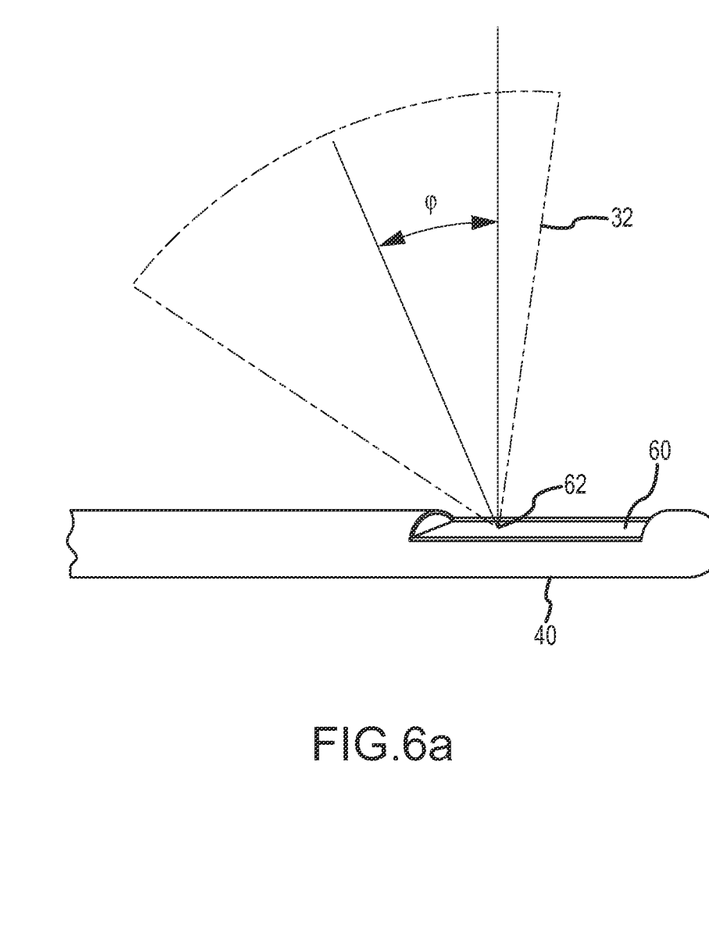
FIG. 6a generally illustrates a representative orientation of the echo plane relative to the ultrasound transducer having both angular and translational error in accordance with an embodiment of the present disclosure.
Figure 6B:
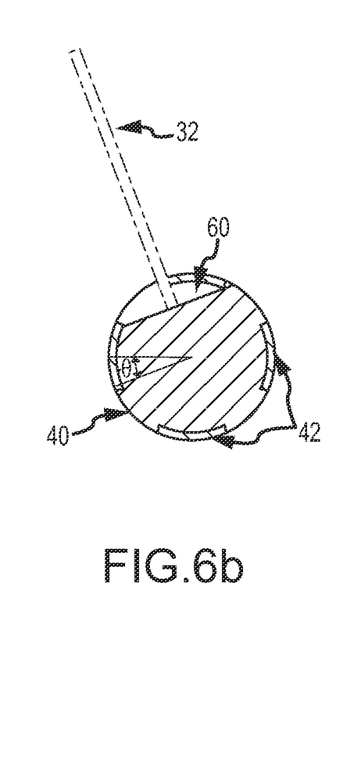
FIG. 6b is a cross-sectional view generally illustrating a representative orientation of the echo plane relative to the electrodes having angular error about the longitudinal axis of the sensor array in accordance with an embodiment of the present disclosure.

As shown in FIGS. 6a and 6b, ultrasound transducers 40 as constructed may have an echo plane 32 that has both translational error and angular error. A translational error is present when the apex 62 of the echo plane 32 does not fall at the specified three dimensional offset from the centroid of the sensor array 38, but rather may be displaced along the longitudinal axis of the sensor array 38 in either a distal or proximal direction. A rotational error can occur when either the positions of the electrodes 42 within the sensor array 38 are rotated about the longitudinal axis of the sensor array 38 relative to the ultrasound transducer face 60, as show in FIG. 6b, or the longitudinal axis of the sensor array 38 is not perpendicular to the echo plane 32 bisector, as shown in FIG. 6a. When combining the ICE image 12 with another imaging modality (e.g., the geometric model 14) compensation for these errors may be employed, several illustrative examples of which are described in detail below.

The electronic control system 22 is configured to acquire the ICE image 12, the geometric model 14, and the electrode position data set 26 having the position and orientation within the geometric model 14 of electrodes 42 detected by the VNM system 20. The ECS 22 is further configured to generate a user interface 16 depicting the ICE image 12 as well as a two dimensional rendering 64 (2D rendering) of the geometric model 14 having the ICE image 12 projected from the location of the ICE catheter 30 within the geometric model 14. The user interface 16 is further configured to contain an electrode registry 66 displaying a listing of the electrode position data set 26 and to receive user input identifying electrodes or other identifiable features appearing in both the ICE image 12 and the geometric model 14. The electrodes appearing in both the ICE image 12 and the geometric model 14 form a fiducial point pair allowing the ECS 22 to adjust the position and orientation of the ICE image 12 projected into the geometric model 14. The ECS 22 may include a programmed electronic control unit (ECU) in communication with a memory or other computer readable media (memory) suitable for information storage. Relevant to the present disclosure, the ECS 22 is configured, among other things, to receive user input from one or more user input devices electrically connected to the system 10 and to issue commands (i.e., display commands) to the display 24 of the system 10 directing the depiction of the user interface 16 to change the perspective of the representation of the geometric model 14 in accordance with the received user input or update the ICE image 12. The ECS may be configured to be in communication with the ICE imaging system 18 and the VNM system 20 to facilitate the acquisition of the ICE image 12 as well as the geometric model 14 and electrode position data set 26. The communication between the ICE imaging system 18 and the VNM system 20 may be accomplished in an embodiment through a communications network (e.g., a local area network or the internet) or a data bus.

It should be understood that although the VNM system 20, the imaging module 34, and the ECS 22 are shown separately, integration of one or more computing functions may result in a system including an ECS 22 on which may be run both (i) various control and image formation logic of the ICE system 18 and (ii) the geometric modeling and position tracking functionality of the VNM system 20. For purposes of clarity and illustration only, the description below will be limited to an embodiment wherein the ECS 22 is configured to perform the location and orientation of the echo plane 32, and thereby the ICE image 12, within the geometric model 14 and apply one or more calibration steps to correct the position and orientation of the projected ICE image 12 within the geometric model 14 in response to received user input. It will be appreciated, however, that in other exemplary embodiments, the ECS 22 may be configured to generate the ICE image 12 from data representing ultrasound energy received by the ultrasound transducer 40 and to generate the geometric model 14 from response signals generated by electrodes 42 of medical devices responsive to the electric fields of the VNM system 20. This arrangement remains within the spirit and scope of the present disclosure.

The position and orientation of the ICE catheter 30 within the geometric model 14 may be determined in six degrees of freedom by the ECS 22 when the sensor array 38 contains at least three electrodes 42 having electrical positions 50 that are not collinear, thereby defining a plane in space. The known physical dimensions between the electrodes 42 within the sensor array 38 allow the ECS 22 to identify the corresponding spacing pattern between the electrical positions 50 contained in the electrode position data set 26, thereby identifying the points defining a plane to orient the ultrasound transducer 40 within the geometric model 14. The ECS 22 may orient the echo plane 32 using the known offset distance from the echo plane 32 to the sensor array 38. The centroid location may be determined from the known physical spacing and orientation of the electrodes 42, and thereby the corresponding electrical positions 50. An exemplary method of locating a catheter using non-collinear electrodes of an impedance based system is described in detail in U.S. patent application Ser. No. 12/347,271, referenced previously.

When the echo plane 32 has been oriented in the geometric model 14 the ECS 22 may generate a transformation function allowing a coordinate within the geometric model 14 to be quickly calculated for each point in the image data set of the ICE image 12, thereby allowing the ICE image 12 to be projected (e.g., displayed) within the geometric model 14. When an ICE catheter 30 contains more than three electrodes 42, such as for generating electrogram signals 52, the determination of the position and orientation of the echo plane 32 by the ECS 22 becomes more robust as the electrical positions 50 of the additional electrodes 42 allow the ECS 22 to compensate for non-functioning electrodes 42 or to reject errant position response signals 44.

Figure 7:
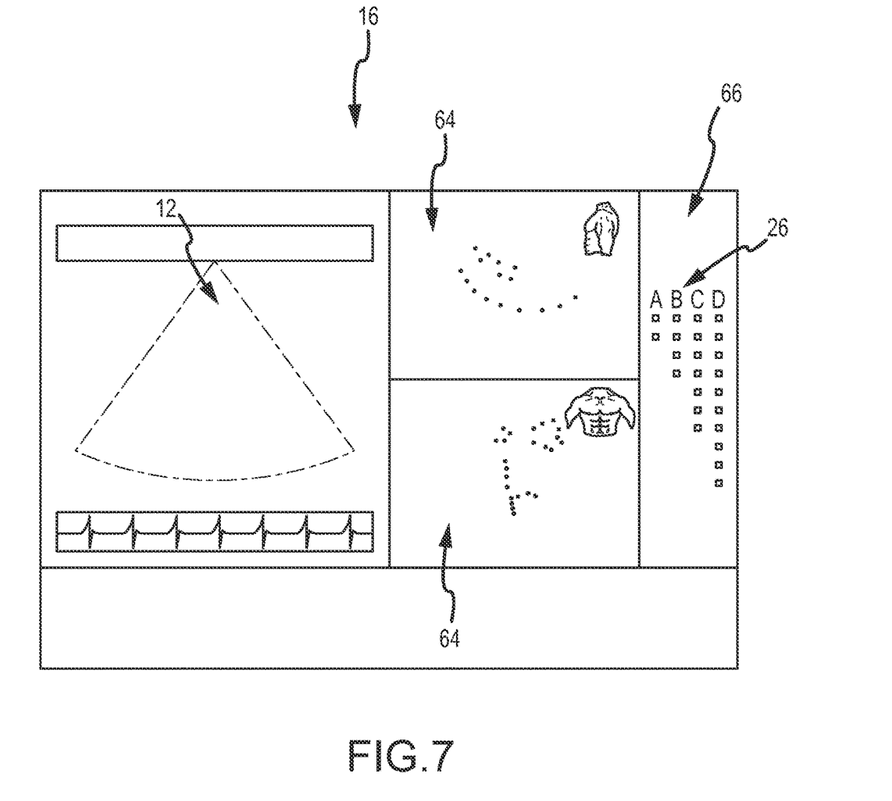
FIG. 7 illustrates an exemplary diagrammatic representation of an interface window for receiving user input identifying fiducial point pairs in accordance with an embodiment of the present disclosure.

The ECS 22 is further configured to generate a user interface 16 and exemplary embodiment of which is illustrated in FIG. 7, depicting the ICE image 12, a 2D rendering 64 having the ICE image 12 projected therein, an electrode registry 66 listing or displaying the detected electrodes from medical devices within the geometric model 14. The user interface 16 is further configured to allow the user to identify one or more fiducial point pairs by selecting an electrode from the electrode registry 66 and then identifying a corresponding point within the ICE image 12. The user 28 may identify a series of fiducial point pairs in this manner. As fiducial point pairs are identified, the ECS 22 may apply calibration steps adjusting the position, orientation, and display of the ICE image 12 within the geometric model 14 to correct for angular and translational errors in the projection of the ICE image 12 from distortion effects caused by variations in catheter 30 devices and by non-homogenous electrical properties that may occur in the body.

When the angular and translational error for the ICE catheter 30 are unknown the archetypal orientation of the echo plane 32 and the ultrasound transducer 40 of FIGS. 5a and 5b can be used to determine the projected coordinate of a point in the ICE image 12 by locating the origin of the ICE image data set at the apex 62 of the archetypal orientation (e.g, centered along the axial length of the transducer face 60). However, the projected location for an identified feature in the ICE image 12 is unlikely to correspond precisely with the position of the feature within the geometric model 14 because of the positional uncertainties.

The positional uncertainties created by translational and angular errors associated with a given ultrasound transducer as well as localized impedance variations effecting the VNM system 20, and thereby the geometric model 14, can be corrected through the use of fiducial point pairs. As described above, fiducial point pairs can be created for objects or structures identifiable in both the ICE image 12 and the geometric model 14. Fiducial point pairs can be anatomical structures, static catheter electrodes 42, or electrodes 42 temporarily positioned near a structure of interest. Fiducial point pairs have two components, the first being the coordinates corresponding to the identified structure within image data set of the ICE image 12, and the second component being the coordinates of the identified structure within the geometric model 14. Once identified, the first component point can be displayed within the ICE image 12 projected in the geometric model 14.

In one embodiment, the first and second component points of a fiducial point pair are displayed in the same color within the user interface 16 so as to make them easily identifiable as a fiducial point pair. When both the first and second component points of a fiducial point pair are displayed in the 2D rendering 64, the component points may be displayed with a line joining the components. The length of the line serves as an approximation of the error present in the position of the ICE image 12 within the geometric model 14. The calibration feature of the present disclosure attempts to minimize the positioning error by applying one or more calibration steps.

When a limited number of fiducial point pairs are present some calibration can be performed, and as the number of fiducial point pairs increases the calibration increases in effectiveness.

When only one fiducial point pair has been identified, adequate calibration can be accomplished when distance scaling between the image data set coordinates and the geometric model 14 is known to be accurate (e.g., the transformation function does not involve scaling), or where the translational error is known to be small.

When distance scaling is accurate the calibration is accomplished by first translating the coordinates of the projected image data set until the projected coordinate of the first fiducial component point (i.e., the projected coordinate of the user identified point from the ICE image) are an equivalent distance as the second fiducial component (i.e., the geometric model position) from the position of the apex 62 of the archetypal orientation shown in FIGS. 5a and 5b. The translation is followed by rotating the projected image data set about the apex 62 until the projected position of the first fiducial component and position of the second fiducial component are substantially the same within the geometric model 14.

When translation error is known to be small, a calibration step may be accomplished by rotating the projected coordinate of the first fiducial component about either the position of the apex 62, shown in FIG. 6a as angle $\phi$, or the longitudinal axis of the sensor array, shown in FIG. 6b as angle $\theta$, until the projected coordinate of the first fiducial component is intersected by a ray extending from the apex 62 of the ultrasound transducer 40 to the second fiducial component. Once all three points are intersected by the ray a scaling factor correcting the position of the projected first fiducial component onto the position of the second fiducial component may be applied to the projected coordinates of the image data set to correct the distance discrepancies of the projected ICE image 12.

Theses single point calibrations can be applied successively as additional fiducial point pairs are identified, and such iterative corrections can approach the solution reached by a single step calibration involving all points. It should be understood that even though the calibration operations have been described as relative to the apex 62 shown in FIG. 5a, other points may be used as the origin of calibration if more appropriate, such as the centroid of the sensor array 38 or the origin of the geometric model 14. Such choices for the calibration frame remain within the spirit and scope of the present disclosure.

When three or more fiducial point pairs have been identified calibration may be accomplished by calculating a homogeneous transformation matrix that minimizes the distance between fiducial components. The homogeneous transformation matrix corrects for both rotation and translational misalignment, and is a form of the Procrustes problem, which has well known solutions to those skilled in the art.

In some instances, orthogonal rotation matrices produced by Procrustes solutions may produce a mirror reflection or rotation causing a right handed coordinate system to become left handed, resulting in a large positioning error due to an axis being reversed in space. Such axis reversal may be eliminated through the use of redundant electrodes 42. In an alternative embodiment, a unit quaternion orientation solution may be utilized rather than, or in addition to, redundant electrodes 42 to maintain the handedness of the coordinate system. The unit quaternion solution is restricted to true rigid body rotation and thus correspond to special orthogonal rotational matrices. An exemplary unit quaternion approach involving a non-linear least squares solved directly by means of an eigenvalue determination is described in Kearsley, Simon, 1989. On the orthogonal transformation used for structural comparisons. Acta Cryst. A45:208-210, which is incorporated herein by reference in its entirety.

Whether an orthogonal matrix or unit quaternion approach is used to solve for the transform resulting in the best matching orientation, it is useful to track the quality of this determination through residual error to the fit. When electrical noise such as a pacing artifact temporarily disturbs the solution for the catheter's position and orientation it often results in high residual error. In an alternative embodiment, the ECS 22 may be configured to temporarily cease projection of the ICE image 12 within the geometric model 14 or generate an alternative visual notification within the user interface 16 when a high residual error is produced during a calibration step or at other times when the ICE catheter's position and orientation are being determined.

Once the homogenous transformation matrix has been obtained it can be used as the transformation function to project any coordinate from the ICE image 12 into the geometric model 14. The location of fiducial point pairs affect the homogeneous transformation matrix solution and areas of the model farther from the selected fiducial point pairs may suffer from extrapolation error due to non-homogeneous electric fields. By selecting fiducial point pairs near an area of interest, such as where an ablation procedure will be performed, this extrapolation error can be minimized.

When four or more fiducial point pairs are identified calibration can include scaling and non-orthogonal translations, and when twelve or more fiducial point pairs are known the calibration corrections can employ more general affine transformations.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An intracardiac echo catheter comprising:
a flexible member having a distal end and a proximal end;
a sensor array having an ultrasound transducer and at least three electrodes being attached to the distal end, wherein each of the at least three electrodes comprises an electrical position and a physical position, and wherein the electrical position comprises a further radial distance from a longitudinal axis of the sensor array than a radial distance of the physical position for at least one of the at least three electrodes, each of the electrodes configured to generate a position signal in response to an electric field, the electrodes being arranged such that positions indicated by the position signals are not collinear and are not orthogonal; whereby the position signals allow a visualization, navigation, or mapping system to locate and orient the catheter in space.

2. The catheter of claim 1, having at least one of the at least three electrodes positioned distal to the ultrasound transducer and having one of the at least three electrodes positioned proximal to the ultrasound transducer.

3. The catheter of claim 1, wherein at least one of the electrodes is a ring electrode.

4. The catheter of claim 1, wherein at least one of the electrodes is a spot electrode.

5. The catheter of claim 1, wherein at least one of the electrodes is a ring electrode having a portion of a conductive surface of the electrode insulated so as to be non-conductive.

6. The catheter of claim 1, each of the electrodes being further configured to generate an electrogram of cardiac structures in close proximity thereto.

7. An elongate medical device comprising:
a flexible member having a distal end portion and a proximal end portion;
an ultrasound transducer disposed at the distal end portion of the flexible member; and
at least three electrodes disposed in a non-collinear and non-orthogonal configuration at the distal end portion of the flexible member, wherein each of the at least three electrodes comprises an electrical position and a physical position, and wherein the electrical position comprises a further radial distance from a longitudinal axis of the flexible member than a radial distance of the physical position for at least one of the at least three electrodes, each of the electrodes configured to generate a position signal in response to an electric field.

8. The elongate medical device of claim 7, wherein a first one of the at least three electrodes is a first spot electrode.

9. The elongate medical device of claim 8, wherein a second one of the at least three electrodes is a second spot electrode.

10. The elongate medical device of claim 9, wherein a third one of the at least three electrodes is a ring electrode.

11. The elongate medical device of claim 9, wherein the first spot electrode is disposed at a different circumferential position of the flexible member than the second spot electrode.

12. The elongate medical device of claim 7, wherein a first of the at least three electrodes is distal of the ultrasound transducer and a second of the at least three electrodes is proximal of the ultrasound transducer.

13. The elongate medical device of claim 7, wherein at least one of the at least three electrodes is partially masked.

14. The elongate medical device of claim 7, wherein at least one of the at least three electrodes is disposed behind the ultrasound transducer.

15. The elongate medical device of claim 7, wherein the at least three electrodes are evenly spaced about the circumference of the flexible member.

16. A system comprising:
an elongate medical device comprising:
a flexible member having a distal end portion and a proximal end portion;
an ultrasound transducer disposed at the distal end portion of the flexible member, the ultrasound transducer associated with an ultrasound imaging plane;
at least three electrodes disposed in a non-collinear and non-orthogonal configuration at the distal end portion of the flexible member, wherein each of the at least three electrodes comprises an electrical position and a physical position, and wherein the electrical position comprises a further radial distance from a longitudinal axis of the flexible member than a radial distance of the physical position for at least one of the at least three electrodes, each of the electrodes configured to generate a position signal in response to an electric field; and an electronic controller comprising a processor, the electronic controller configured to receive or determine respective electrical positions of the at least three electrodes and to determine a position and orientation of the ultrasound imaging plane according to the respective electrical positions of the at least three electrodes.

17. The system of claim 16, wherein the electronic controller is further configured to display an image from the ultrasound transducer with respect to an anatomical model according to the determined position and orientation of the ultrasound imaging plane.

18. The system of claim 16, wherein the electronic controller is further configured to receive electrograms captured with the at least three electrodes and to cause the electrograms to be displayed for a user.

19. The system of claim 16, wherein at least one of the at least three electrodes is a ring electrode.

20. The system of claim 16, wherein a first one of the at least three electrodes is disposed proximal of the ultrasound transducer and a second one of the at least three electrodes is disposed distal of the ultrasound transducer.

* * * * *